United States Patent [19]

Müller et al.

[11] 4,175,839
[45] Nov. 27, 1979

[54] SLIT-LAMP APPARATUS

[75] Inventors: Ortwin Müller, Lorch; Karl Grünvogel, Aalen; Kurt Schulz, Oberkochen, all of Fed. Rep. of Germany

[73] Assignee: Carl Zeiss-Stiftung, Oberkochen, Fed. Rep. of Germany

[21] Appl. No.: 843,236

[22] Filed: Oct. 18, 1977

[30] Foreign Application Priority Data

Oct. 23, 1976 [DE] Fed. Rep. of Germany ....... 7633232

[51] Int. Cl.$^2$ .......................... A61B 3/10; A61B 3/00; A61B 9/00
[52] U.S. Cl. .......................................... 351/14; 351/9; 351/38
[58] Field of Search ..................... 351/14, 9, 6, 11, 38, 351/16; 73/80; 350/39, 254, 175 ML

[56] References Cited

U.S. PATENT DOCUMENTS

| | | | |
|---|---|---|---|
| 2,155,171 | 4/1939 | Ronne | 351/11 X |
| 2,940,357 | 6/1960 | Oswold | 351/16 |
| 3,693,416 | 9/1972 | Dianetti | 351/14 X |
| 4,101,201 | 7/1978 | Tojyo | 350/175 ML |

FOREIGN PATENT DOCUMENTS 1399499  4/1965  France ...................................... 351/14

*Primary Examiner*—John K. Corbin
*Assistant Examiner*—Rodney B. Bovernick
*Attorney, Agent, or Firm*—Hopgood, Calimafde, Kalil, Blaustein & Lieberman

[57] ABSTRACT

The invention contemplates slit-lamp apparatus for ophthalmological examinations and is characterized by simplicity of components designed to facilitate use, the use being assumed to involve the analytical operations most often needed. The instrument is portable and provides ready availability of slit-projector means and tonometer means when desired, on the microscope-viewing axis. All components are upstanding, with respect to the mounting base, and simple knurled-ring adjustments enable selection of projected-slit dimensions and filters.

7 Claims, 4 Drawing Figures

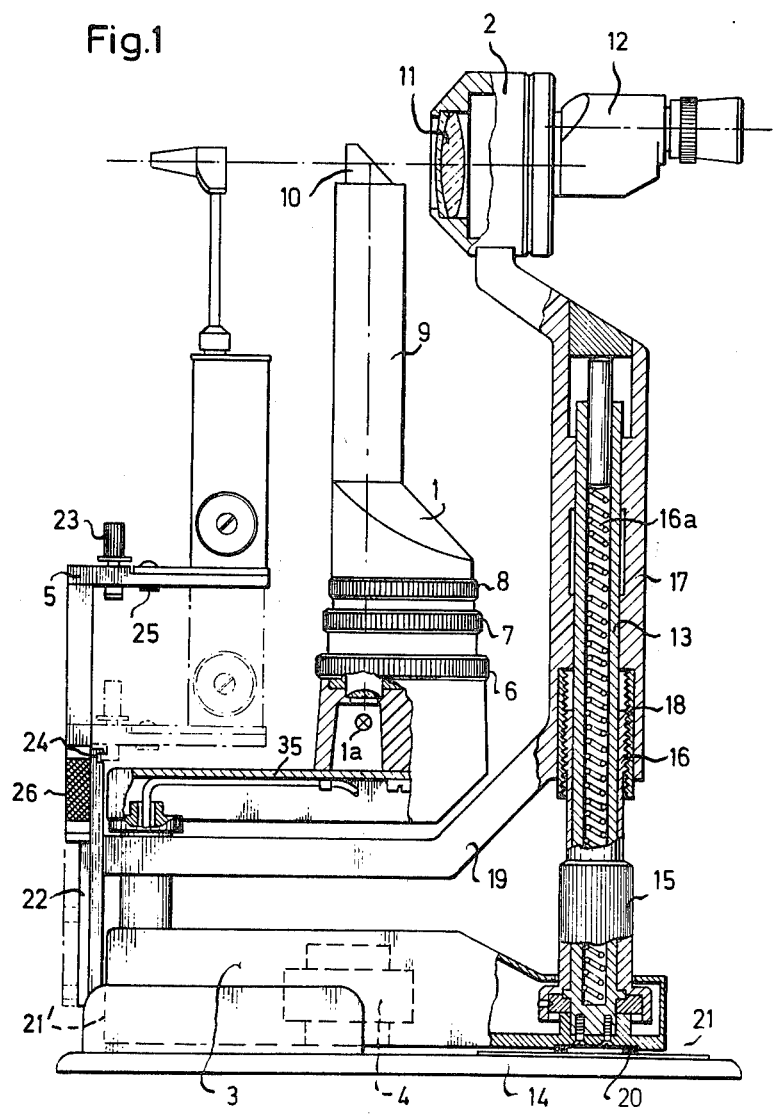

SLIT-LAMP APPARATUS

The present invention relates to a slit lamp for ophthalmological examinations and comprises a slit projector, a microscope, an instrument base, a power pack, and a tonometer support.

Conventional slit lamps are so constructed as to permit the conduct of practically all known methods of examination of the clinical and practicing ophthalmologist. They represent universal instruments which are of complicated optical and mechanical construction. The dimensions of these universal instruments are correspondingly large.

The object of the present invention is to provide a slit lamp with which only the most frequently effected examinations are possible and which is therefore smaller in dimension and affords a large working space between doctor and patient.

Another object of the invention is to arrange all the manipulating elements in such a way that they are conveniently accessible, thereby obtaining an improvement in the corresponding functions as compared with conventional slit lamps.

In accordance with the invention, these objects are achieved by providing the slit projector with a rotatable disc having discrete slit diaphragms of different width, by providing the microscope with an achromatic main objective and a binocular straight tube of short structural length, by securing a guide column in the foundation plate of the instrument base, there being provided, coaxially within the guide column, manipulating elements for horizontal and vertical movement of the slit lamp, by installing in the instrument base the power supply transformer for the slit lamp, and by providing a vertically displaceable tonometer support in the free space which exists between the doctor and the patient.

In a preferred embodiment of the invention, eight discrete slit diaphragms, with slit widths of 0.1 to 5 mm, produced by photochemical or photomechanical reproduction methods, are arranged on a disc and can be swung into the ray path of the slit projector.

For the adjustment of slit height, it is advantageous to rotatably position a trumpet-shaped diaphragm in the ray path of the slit projector.

For special examinations or to increase contrast, it is advisable to arrange color filters on a rotatable disc and to swing them into the ray path of the slit projector.

The manipulating elements for adjustment of slit width and slit height, and for selection of the filter to be used, are preferably coaxial knurled discs of different outside diameter.

In a preferred embodiment of the invention, a tonometer support is arranged for vertical displacement in a guide, the tonometer being capable of being fixed in the upper end position of the guide in its position of use and of being located at the lower stop of the guide in its position of rest.

The advantages obtained with the present invention reside, in particular, in the fact that the user obtains manipulation and work space which was not previously present in slit lamps, and that an applanometer of traditional construction can be left permanently in the space between microscope and patient without interfering with the method of examination customary for the apparatus. Further advantages reside in the readily accessible arrangement of all operating elements, enabling dependable and rapid operation both for right-handed and for left-handed persons. By reduction of the functional elements to those involved in the most frequent applications, the slit lamp of the invention furthermore is now within a price range which is of interest to the practicing ophthalmologist.

One example of the invention is shown in the drawing and will be described in further detail below.

FIG. 1 is a view in side elevation of a slip lamp of the invention, certain parts being broken away and in longitudinal section;

Figure 4:
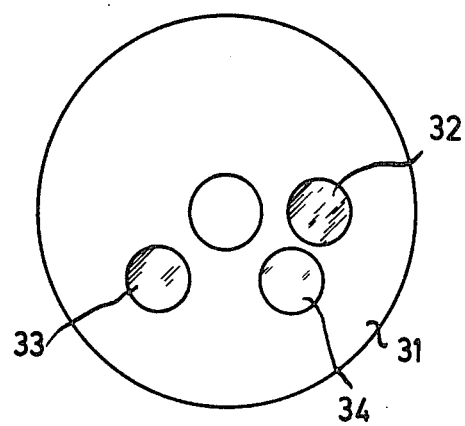
FIG. 4 is a plan view of a filter carrier, for use in the slit projector.

In the partially sectioned view of the invention shown in FIG. 1, 1 is the slit projector, 2 the microscope, 3 the instrument base, 4 the power pack, and 5 the tonometer support. The slit projector 1 includes a light source 1a and three knurled operating discs or rings 6-7-8, for selection of slit width, slit height, and the different filters, are arranged coaxially and by a difference in their outside diameters, assure reliable and rapid operation for both right-handed and left-handed persons. Flexible electrical leads to lamp 1a pass from powerpack 4 via hollow support and connecting elements. When using the lower knurled disc 6, eight discrete slit widths, ranging from 0.1 to 5 mm can be set; the correct slit setting is assured by detent means, which can be easily sensed. When using the knurled disc 7, slit height can be continuously adjusted from 0.1 to 8 mm, by means of the trumpet-shaped diaphragm shown in FIG. 3; the knurled disc 7 has a right-hand stop, at which position a horizontal slit of 0.1 mm width is projected. The slit diaphragm and the trumpet-shaped diaphragm are arranged on metal foils or glass plates and can be produced by different methods of reproduction (for instance, copper-etching). Various filters, such as green or blue filters, can be interposed in the ray path by means of the knurled ring 8. Furthermore, to examine for pupil reaction, the disc moved by the knurled ring 8, shown in FIG. 4, can be brought into a detent-held position in which the illumination in interrupted. A narrow tube 9 on the projection axis of source 1a mounts the deflection prism 10 of the slit projector and is eccentric to the rotary axis of the operating knurled discs 6-7-8. In a commercial embodiment, the distance between the axis of tube 9 (or optical axis) and the eye of the patient is 96 mm, thus affording the doctor practically unimpeded space for this manipulations.

The microscope 2 consists of an achromatic principal objective 11 and a binocular straight tube 12 which is of particularly short structural length. The distance between the exit pupil and the eye of the patient is thereby considerably reduced. The microscope magnification is preferably 12.5, being the one most frequently required as standard enlargement in actual practice; however, the mechanical and optical construction is such that, if necessary, a rapid magnification changer can be interposed as attachment between objective and tube. It is then possible to have enlargements of 7.5 x, 12.5 x, and 19 x.

The operating element 15 for horizontal movement and vertical displacement of the slit lamp is arranged in the instrument base 3, coaxial to the guide column 13. Guide column 13 is fastened in the foundation plate 14 of the instrument base 3, and the adjustment element 15 for horizontal and vertical movement is supported on the lower half of the column. The upper region of the column 13 serves as guide means for the vertical movement. Within the column, there is a compression spring 16a of very linear characteristic, which practically completely compensates for the weight of the instrument. The power pack 4 serving source 1a is mounted in the free space of the instrument base 3; thus, the slit lamp is a portable independent unit which need merely be connected to an electrical outlet.

In use, vertical displacement of the instrument is effected by turning the operating element 15. Operating element 15 includes, at its upper part, an external thread 16 which engages in the internal thread 18 of the column part, thus enabling conversion of rotation of element 15 into vertical movement of the column part 17. A lever or offset arm 19 connects slit projector 1 and the tonometer support 5 with column part 17 (which carries microscope 2), so that microscope 2, slit projector 1, and the tonometer move together in the same vertical movement. A vertical guide rod 19' carried by arm 19 is slidable in a guide bore in the instrument base 3, to assure against rotation of arm 19, and the slit-projector 1 is mounted at the free end of a second arm 35, the latter being pivotable about the axis of rod 19' to enable slit-projection to be selectively placed on or off the microscope axis. Horizontal movement of the instrument is conveniently introduced by grasping the operating element 15 and by simply pushing the instrument, it being noted that on the foot of the guide column 13 there is arranged a friction plate 20 or a hemisphere which slides on the base or platform 21. It will be understood that carriage guide means of known construction (suggested at 21') can serve to assure precise horizontal movement.

As a result of the compact arrangement of the basic units of the slit lamp of the invention there is produced, between the patient and the doctor, a free space not present in the case of conventional slit lamps, this space being suitable to receive a tonometer. The tonometer support 5 is adjustably fastened on a vertical guide rail 22. In order to effect tonometric measurements, the instrument is brought into position of use by an upward displacement of about 60 mm along the guide rail 22, to the position shown in full lines in FIG. 1. For this purpose a lock 23 (which retains the retracted position, shown in phantom outline) is released from the detent 24. In its position of use, the tonometer support is held fast by suitable means 26. If no tonometric measurements are intended, the tonometer can be detached from its connection to the tonometer support 5, at nipple 25.

Figure 2:
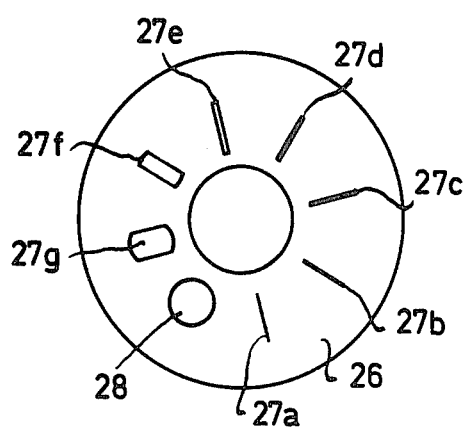
FIG. 2 is a plan view of a slit diaphragm with discrete slit widths, for use in the slit projector.

In FIG. 2, the disc actuated by the knurled ring 6 is seen to have seven slit diaphragms 27a–27g and an opening 28 for free passage of projected light.

Figure 3:
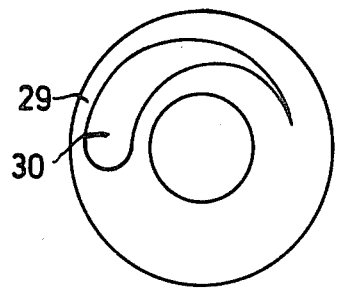
FIG. 3 is a plan view of a trumpet-shaped diaphragm for adjustment of slit heights, contained in the slit projector.

In FIG. 3, the disc 29 is shown to include the trumpet-shaped diaphragm 30 for limiting the slit heights. This disc can be operated by the knurled ring 7; and it will be understood that upon the rotation of the knurled ring 7 the trumpet-shaped diaphragm 30 is rotated over the selected slit diaphragm.

FIG. 4 is a plan view of the disc 31 which is actuated by the knurled ring 8 and which carries the filters. For instance, a green filter 32 and a blue filter 33 may be provided, as well as an opening 34 for the unfiltered passage of the illuminating beam.

What is claimed is:

1. Slit lamp for ophthalmological examinations, consisting of a slit projector, a microscope, an instrument base, a power pack and a tonometer support, characterized by the fact that the slit projector includes a plurality of discrete slit diaphragms of different width arranged on a rotatable disc for selective placement in the ray path of the slit projector and that, in order to adjust the height of slit, a trumpet-shaped diaphgram is arranged rotatably in the ray path of the slit projector, that the microscope consists of an achromatic principal objective and a binocular straight tube of short structural length, that a guide column is fastened in the foundation plate of the instrument base, and operating elements for the horizontal and vertical movement of the slit lamp are provided coaxial to the guide column, that the power pack for the slit lamp is installed in the instrument base, and that a tonometer support which is adjustable in height is provided in the free space thus resulting between the doctor and the patient.

2. Slit lamp according to claim 1, characterized by the fact that color filters are arranged on a rotatable disc for selective placement in the ray path of the slit projector.

3. Slit lamp according to claim 2, characterized by the fact that the operating elements for setting the slit width, the slit height, and the filter to be used are arranged as coaxial knurled discs.

4. Slit lamp according to claim 1, characterized by the fact that the tonometer support is axially displaceable in a guide, the tonometer being adapted to be fixed in position of use in the upper end position of the guide and being in position of rest when it is against the lower stop of the guide.

5. Slit-lamp apparatus for ophthalmological examinations, comprising a base, an upstanding guide column fixed to said base, a vertical slide guided by said column and including microscope-support means at its upper end and a first offset arm at its lower end, adjustable means for selectively elevating said slide with respect to said base, vertical guide means coacting between said base and said offset arm for holding said offset arm against rotation about the column axis, a microscope mounted by said support means and comprising an achromatic principal objective with its axis oriented horizontally, said microscope including a binocular straight tube of short structural length, a second offset arm pivotable about a vertical axis near said vertical guide means and carried by said first offset arm, said second offset arm being selectively pivotable about its axis and through a range of positions in and out of the vertical plane defined by and between the axes of said vertical guide means and of said column, slit-projector means vertically mounted at the offset end of said second arm, said slit-projector means including a light source and slit-diaphragm means on a vertical optical axis, said slit-diaphragm means comprising a first rotatable disc including a plurality of slit diaphragms for selective placement in the ray path of the slit projector and a second rotatable disc including a trumpet-shaped diaphragm for selective positioning in the ray path of the slit projector to adjust the height of the slit, a prism on said vertical optical axis at the upper end of said projector means and adapted to fold the slit-projection axis onto the microscope objective axis when said second arm is pivoted into the path of microscope viewing, and tonometer-support means including vertically adjustable means carried at the offset end of said first arm.

6. Slit-lamp apparatus according to claim 5, in which said vertical guide means includes a guide rod carried by said first offset arm and slidable in a guide bore in said base, said second offset arm being pivotably supported on the axis of said rod.

7. Slit-lamp apparatus according to claim 5, in which said rod is tubular, and in which flexible electrical-supply means for said lamp pass from said base and through said rod.

* * * * *